United States Patent
Lei et al.

(10) Patent No.: US 11,851,405 B2
(45) Date of Patent: Dec. 26, 2023

(54) METHOD FOR PREPARING DIALKYL CARBONATE BY ALCOHOLYSIS OF UREA

(71) Applicants: Yongcheng Lei, Chengdu (CN); Yongzhong Lei, Chengdu (CN)

(72) Inventors: Yongcheng Lei, Chengdu (CN); Yongzhong Lei, Chengdu (CN); Qinghong Lv, Zhongshan (CN); Yu Wang, Luzhou (CN)

(73) Assignees: Yongcheng Lei, Chengdu (CN); Yongzhong Lei, Chengdu (CN)

( * ) Notice: Subject to any disclaimer, the term of this patent is extended or adjusted under 35 U.S.C. 154(b) by 521 days.

(21) Appl. No.: 16/966,011

(22) PCT Filed: Mar. 16, 2018

(86) PCT No.: PCT/CN2018/079330
§ 371 (c)(1),
(2) Date: Jul. 30, 2020

(87) PCT Pub. No.: WO2019/148604
PCT Pub. Date: Aug. 8, 2019

(65) Prior Publication Data
US 2020/0354305 A1   Nov. 12, 2020

(30) Foreign Application Priority Data
Feb. 1, 2018 (CN) .......................... 201810102903.9

(51) Int. Cl.
*C07C 68/00* (2020.01)
(52) U.S. Cl.
CPC ................................. *C07C 68/00* (2013.01)
(58) Field of Classification Search
CPC ........................................................ C07C 68/00
See application file for complete search history.

(56) References Cited

U.S. PATENT DOCUMENTS

| | | |
|---|---|---|
| 5,902,894 A | 5/1999 | Ryu |
| 5,980,445 A | 11/1999 | Mizukami et al. |
| 6,031,122 A | 2/2000 | Mizukami et al. |
| 6,392,078 B1 | 5/2002 | Ryu et al. |

FOREIGN PATENT DOCUMENTS

| | | |
|---|---|---|
| CN | 1416949 A | 5/2003 |
| CN | 1428329 A | 7/2003 |
| CN | 1431190 A | 7/2003 |
| CN | 101659616 A | 3/2010 |
| CN | 102909076 A | 2/2013 |
| CN | 104549439 A | 4/2015 |
| CN | 107973728 A | 5/2018 |

OTHER PUBLICATIONS

Ball et al., Carbonates and Polycarbonates from Urea and Alcohol, Angew. Chem. Int. Ed. Engl. 19 (1980) No. 9, pp. 718-720 (Year: 1980).*
Yang et al. Synthesis of dimethyl carbonate from urea and methanol catalysted by the metallic compounds at atmospheric pressure, Catal. Commun. 7 (2006), pp. 472-477 (Year: 2006).*
Paquin, Über Umsetzungen von Harnstoff mit Alkoholen, Z. Naturforschg. 1, 518-523 (1946) (Year: 1946).*
Zhao et al., Synthesis of Dimethyl Carbonate from Methyl Carbamate and Methanol with Zinc Compounds as Catalysts Ind. Eng. Chem. Res. 2008, 47, 5913-5917 (Year: 2008).*
Huang et al. Chem. Soc. Rev., 2015, 44, 3079-3116 (Year: 2015).*
Peter Ball et al., Synthesis of Carbonates and Polycarbonates by Reaction of Urea With Hydroxy Compounds, C1 Mol. Chem., 1984, pp. 95-108, vol. 1.

* cited by examiner

*Primary Examiner* — Michael Barker
*Assistant Examiner* — Jed A Kucharczk
(74) *Attorney, Agent, or Firm* — Bayramoglu Law Offices LLC

(57) ABSTRACT

A dialkyl carbonate is prepared by reacting urea with an alkyl monohydric alcohol at 70° C. to 150° C. under normal pressure or reduced pressure. The reaction is conducted for 6 h to 30 h under stirring and reflux, with one or more of magnesium, calcium, aluminum, chromium, manganese, iron, cobalt, nickel, copper and zinc as a primary catalyst and one or more compounds including an electron-donating nitrogen, phosphonis, oxygen or sulfur atom as a catalyst promoter. The dialkyl carbonate is prepared under low reaction temperature and normal pressure or reduced pressure, with high selectivity and high yield. With simple operations, high safety and low cost for the process, the method has prominent industrial application prospects.

5 Claims, No Drawings

METHOD FOR PREPARING DIALKYL CARBONATE BY ALCOHOLYSIS OF UREA

CROSS REFERENCE TO THE RELATED APPLICATION

This application is the national phase entry of International Application No. PCT/CN2018/079330, filed on Mar. 16, 2018, which is based upon and claims priority to Chinese Patent Application No. 201810102903,9, filed on Feb. 1, 2018, the entire contents of which are incorporated herein by reference.

TECHNICAL FIELD

The present invention relates to chemical synthesis, and more particularly, to a method for preparing a dialkyl carbonate by alcoholysis of urea.

BACKGROUND

Dialkyl carbonates are an important class of compounds. Many have been commercially produced and widely used in the industry. Dimethyl carbonate, for example, which is a green chemical, is an important solvent in the textile industry and battery production industry and can be used as a raw material for the synthesis of a variety of chemicals. It is widely used as a solvent in coatings, paints, lithium batteries and other industries. Dimethyl carbonate is also used as a raw material for the clean production of polycarbonate, methyl carbamate, isocyanate and other products. Dipropyl carbonate is an important solvent in the battery production industry and also an important raw material for synthesis. Dibutyl carbonate is used industrially in the production of diphenyl carbonate and isocyanate. Dioctyl carbonate is an important raw material for emollients and other care products. With the continuous development of industrial technologies, dialkyl carbonates will be more extensively used.

Urea, a commodity chemical, is directly prepared from ammonia and carbon dioxide at 185° C. and 240 atm. Urea, as a raw material for synthesis, has advantages, such as low price, safe operation, easy transportation, and no geographical restrictions. In the process of preparing a dialkyl carbonate by alcoholysis of urea, urea reacts with an alkyl monohydric alcohol to produce a dialkyl carbonate, with a by-product of ammonia that will be fed into a nitrogen fertilizer production system. In essence, this process indirectly uses the reaction of carbon dioxide and alcohol to prepare a dialkyl carbonate. Therefore, this process has broad prospects and has been the focus of attention in the industry.

It has been proposed to react urea with a hydroxyl-containing compound where the catalyst is an organotin compound, such as dibutyldimethoxytin and tetraphenyltin (Bali, Synthesis of Carbonates and Polycarbonates by Reaction of Urea With Hydroxy Compounds, Cl Mol. Chem., pp 95-108, 1984).

U.S. Pat. No. 5,980,445 discloses a process for preparing a dialkyl carbonate by reacting urea with a $C_{3-6}$ alkyl monohydric alcohol in two stages, where the reaction at the first stage is conducted at 100° C. to 200° C., with a system pressure of 0 MPa to 2 MPa; the reaction at the second stage is conducted at 180° C. to 260° C., with a system pressure of 0 MPa to 3 MPa; and the reaction is conducted for 1 h to 20 h. The yield of diisoamyl carbonate prepared by the reaction of urea with isoamyl alcohol can reach 93.7%. However, this patent only mentions the reaction of alcohol with two or less carbon atoms with urea, which has an extremely-low yield.

U.S. Pat. No. 6,031,122 describes a method for preparing a dialkyl carbonate, where urea reacts with $C_{3-6}$ alkyl monohydric alcohol at 175° C. to 230° C. for 4 h to 20 h under normal pressure or low pressure and reflux, with solvents such as alkane and ether that have a boiling point equal to or above 180° C. The optimal yield of dibutyl carbonate prepared by the reaction of urea with butanol can reach 84.6%. As high-boiling alkane, ether and other solvents are added to the system, and the reaction is conducted under normal pressure or low pressure, the by-product of ammonia will be discharged in time, and thus the reaction proceeds smoothly. Moreover, the process has advantages, such as low investment cost on equipment, and safe and convenient operations. However, this process does not involve the reaction of urea with low-boiling methanol or ethanol.

U.S. Pat. Nos. 5,902,894 and 6,392,078 disclose an improved organotin catalyst, where the primary catalyst has a structure of $R_2SnX_2$ (X=Cl, RO, RCOO or RCOS), $R_3SnX$, RSnO, $Ph_{3-q}RSnX_q$, $Ph_{4-q}SnX_q$ or $R_2Sn(OCH_3)_2$ (R=$C_nH_{2n+1}$, q=0, 1 or 2, and n=2 to 12), and the catalyst promoter is an organic compound with an electron-donating oxygen atom, such as triglyme and tetraglyme. In a rectification reactor, the reaction of urea or amino acid methyl ester with methanol to prepare dimethyl carbonate was investigated, with a system pressure of 0.2 MPa to 1.5 MPa, and a reaction temperature of 150° C. to 200° C. The selectivity for dimethyl carbonate can be as high as 98.2%. During the reaction, the generated ammonia is continuously discharged through rectification, and at the same time, the product of dimethyl carbonate in the system is controlled at a low concentration, so as to allow a smooth reaction and reduce the production of by-products. Due to the higher temperature adopted, it is relatively difficult to discharge ammonia in a pressurized device, and methyl N-methyl formate, methylamine and carbon dioxide are detected in the reaction product.

In CN1416949A, a mixed oxide is disclosed as a catalyst, with 1 to 3 metal oxides of lithium, magnesium, nickel, zinc, lead, iron, molybdenum, zirconium or lanthanum, and zinc oxide as the primary catalyst, and the reaction is conducted at 170° C. to 180° C. for 8 h in a high-pressure autoclave, with an optimal yield of 49.7% for dimethyl carbonate.

CN1428329A discloses a method for preparing dimethyl carbonate with urea and methanol, where oxides obtained by calcining the carbonate or hydroxide of alkali metals and alkaline earth metals are adopted as a catalyst, and the reaction is conducted at 120° C. to 240° C. in a high-pressure autoclave for 4 h to 30 h, with an optimal yield of 26.56% for dimethyl carbonate.

CN101659616A describes a method for preparing diethyl carbonate by reacting ethyl carbamate with ethanol, where a composite metal oxide is adopted as a catalyst, and the reaction is conducted at 150° C. to 200° C. for 1 h to 15 h, with a system pressure of 3.01 MPa, and an optimal yield of 19.1% for diethyl carbonate.

In summary, the current processes for preparing a dialkyl carbonate by alcoholysis of urea have the following problems:

(1) The reaction system has a high temperature. The reaction is mostly conducted at 120° C. to 240° C., and especially in the second stage, the reaction is conducted at 170° C. to 260° C. Urea will be partially decomposed at a high temperature. Isocyanic acid and cyanuric acid are produced from the carbamate in the system under the catalyst, and for the reaction of urea with methanol, methyl carbamate and dimethyl carbonate are subjected to methylation to produce methyl AT-methyl formate.

(2) The reaction of urea with low-boiling alcohol is conducted in a pressurized device. In the reaction system of urea with methanol or ethanol, the pressure increase is particularly significant. In the pressurized reaction system, the generated by-product of ammonia cannot be discharged from the system in time and effectively. Ammonia in the system will inhibit the forward movement of the equilibrium reaction. Ammonia can also react with the reaction product of dimethyl carbonate to form methylamine. Furthermore, the pressurized equipment requires high investment and complicated operations.

(3) The reaction of urea with low-boiling methanol or ethanol results in an unsatisfactory product yield.

In view of this, the present invention is specifically proposed.

SUMMARY

The present invention is intended to provide a method for preparing a dialkyl carbonate by alcoholysis of urea, with high selectivity and high yield. Moreover, the method requires simple and safe operations for the process, and low equipment cost, and has prominent industrial application values.

A dialkyl carbonate is prepared by reacting urea with an alkyl monohydric alcohol, including two stages (I) and (II):

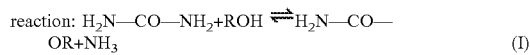

reaction: $H_2N-CO-NH_2+ROH \rightleftharpoons H_2N-CO-OR+NH_3$  (I)

and

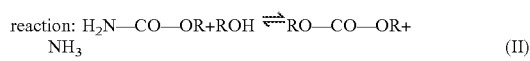

reaction: $H_2N-CO-OR+ROH \rightleftharpoons RO-CO-OR+NH_3$  (II)

where, ROH is the structural formula of the alkyl monohydric alcohol, $R=C_nH_{2n+1}$, and n=1 to 12.

In the reaction stage (I), urea reacts with an alkyl monohydric alcohol to produce carbamate, with a by-product of ammonia. In the reaction stage (II), the carbamate reacts with the alkyl monohydric alcohol to produce a dialkyl carbonate, with a by-product of ammonia. Both (I) and (II) reaction stages, especially the reaction stage (II), are thermodynamically-controlled reactions. Furthermore, reactions at the two stages are reversible, and are influenced by the equilibrium shift.

The same catalyst is adopted in the reactions at the two stages. The reaction at stage (I) is conducted relatively rapidly at a lower temperature and the reaction at stage (II) is conducted relatively slowly at a higher temperature. In order to prevent the occurrence of side reactions, it is necessary to control the reaction system at an appropriate temperature.

In order to realize the objective of the present invention, the inventors provide the following technical solutions in view of the characteristics of the reaction:

(1) The catalyst system used in the reaction consists of a primary catalyst and a catalyst promoter. The primary catalyst includes one or more of magnesium, calcium, aluminum, chromium, manganese, iron, cobalt, nickel, copper and zinc, and the catalyst promoter includes one or more compounds with an electron-donating nitrogen, phosphorus, oxygen or sulfur atom.

(2) The reaction is conducted at a controlled temperature of 70° C. to 150° C.

(3) Under normal pressure or reduced pressure, the reaction system is kept at boil and reflux to continuously remove the generated ammonia from the system.

With the above technical solution, the method for preparing a &alkyl carbonate by alcoholysis of urea provided in the present invention is as follows: A dialkyl carbonate is prepared by reacting urea with an alkyl monohydric alcohol at 70° C. to 150° C. under normal pressure or reduced pressure, where, the reaction is conducted under stirring and reflux, with one or more of magnesium, calcium, aluminum, chromium, manganese, iron, cobalt, nickel, copper and zinc as a primary catalyst, and one or more compounds including an electron-donating nitrogen, phosphorus, oxygen or sulfur atom as a catalyst promoter.

The primary catalyst in the catalyst system specifically includes one or more of chloride, bromide, sulfate, perchlorate, nitrate, and carboxylate $M(RCOO)_q$ (where, M is Mg, Ca, Al, Cr, Mn, Fe, Co, Ni, Cu or Zn, q=2 or 3, $R=C_nH_{2n+1}$, and n=0 to 6) of Mg (II), Ca (II), Al (III), Cr (II, III), Mn (II), Fe (II, III), Co (II), Ni (II), Cu (II) or Zn (II).

The catalyst promoter in the catalyst system includes one or more compounds with an electron-donating nitrogen, phosphorus, oxygen or sulfur atom. The compounds with an electron-donating nitrogen, phosphorus, oxygen or sulfur atom specifically include the followings:

(1) Compounds with an electron-donating nitrogen atom:
(i) Monoamine compound

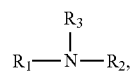

where $R_1$, $R_2$ and $R_3$ are each hydrogen, alkyl or aryl, and there are no more than 20 carbon atoms in $R_1$, $R_2$ and $R_3$;

(ii) alkyl or aryl diamine and triamine compounds, where there are no more than 20 carbon atoms, and specific examples include: ethylenediamine, propanediamine, butanediamine, pentanediamine, hexamethylenediamine, o-phenylenediamine, triethylenediamine, diethylenetriamine or the like; and (iii) nitrogen-containing heterocyclic compounds: pyridine, pyrrole, pyrazole, imidazole, pyrazine, pyridazine, pyrimidine, triazine, 2,4-bipyridine, o-phenanthroline, benzimidazole, benzotriazole, indole, quinoline, pteridine, acridine, phenazine or the like;

(2) Compounds with an electron-donating phosphorus atom:

Trivalent organic phosphine compound

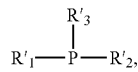

where $R'_1$, $R'_2$ and $R'_3$ are each alkyl or aryl, there are no more than 30 carbon atoms in $R'_1$, $R'_2$ and $R'_3$, and specific examples include: triphenylphosphine, tri(p-tolyl)phosphine, diphenylbutylphosphine, dibutylphenylphosphine, tributylphosphine or the like;

(3) Compounds with an electron-donating oxygen atom:
(i) alkyl or aryl ether, where there are no more than 20 carbon atoms, and specific examples include: dipropyl ether, dibutyl ether, propyl butyl ether, anisole, diphenyl ether, diglyme, triglyme, tetraglyme or the like;

(ii) alkyl or aryl carboxylate ester, where there are no more than 20 carbon atoms;
(iii) alkyl or aryl carboxylate salt, where there are no more than 20 carbon atoms, and the metal is an alkali metal, such as sodium and potassium; and
(iv) oxygen-containing heterocyclic compound: furan, pyran, tetrahydrofuran, tetrahydropyran or the like;
(4) Compounds with an electron-donating sulfur atom:
(i) Alkyl or aryl sulfide, where there are no more than 20 carbon atoms, and specific examples include: dipropyl sulfide, dibutyl sulfide, diphenyl sulfide or the like; and
(ii) sulfur-containing heterocyclic compound: thiophene, bithiophene, benzothiophene or the like;
(5) Compounds with two or more of an electron-donating nitrogen atom, phosphorus atom, oxygen atom and sulfur atom:
(i) Amino acid: glycine, alanine, valine, leucine, isoleucine, serine, threonine, cysteine, methionine, asparagine, glutamine, aspartic acid, glutamic acid, lysine, arginine, phenylalanine, tyrosine, tryptophan, histidine, proline or the like;
(ii) amino (amine) carboxylic acid: aminodiacetic acid, aminotriacetic acid, ethylenediaminetetraacetic acid, diethylenetriaminepentaacetic acid, triethylenetetraaminehexaacetic acid or the like;
(iii) amino (amine) phosphonic acid: aminotrimethylene phosphonic acid, ethylenediaminetetramethylene phosphonic acid, diethylenetriamine pentamethylene phosphonic acid, hexamethylenediamine tetramethylene phosphonic acid, dihexenetriamine pentamethylene phosphonic acid or the like; and
(6) heterocyclic compound with two electron-donating atoms: thiazole, benzothiazoie, morpholine, oxazole, phenothiazine or the like.

The primary catalyst and the catalyst promoter in the catalyst system have a mass ratio of 1:(1-20), and preferably of 1:(1-10).

The urea and the alkyl monohydric alcohol (raw materials in the reaction) are used at a molar ratio of 1:(2-10), and preferably of 1:(4-8).

The catalyst has a mass 5% to 40% and preferably 10% to 30% of that of the urea.

The reaction at stage (I) is conducted at 70° C. to 150° C., and the reaction at stage (II) is conducted at 100° C. to 150° C.

The reaction at stage (I) is conducted for 2 h to 10 h, and the reaction at stage (II) is conducted for 4 h to 20 h.

The urea reacts with ROH (R=$C_nH_{2n+1}$, and n=1 and 2) at boil and reflux under normal pressure. Since methanol and ethanol are low-boiling alcohols and have a relatively-high solubility for ammonia, a solvent is added to the reaction system to increase the temperature of the reaction system and reduce the solubility of ammonia in the system. The solvent added is specifically: one or more of $C_{8-18}$ alkane, toluene, xylene, biphenyl, diphenyl ether, diglyme, triglyme, tetraglyme, sulfolane and dimethyl sulfone. The solvent and the urea are added at a mass ratio of (1-20):1, and preferably of (4-10):1.

The urea reacts with ROH (R=$C_nH_{2n+1}$, and n=3 to 5) at boil and reflux under normal pressure.

The urea reacts with ROH=$C_nH_{2n+1}$, n=6 to 12) at boil and reflux under vacuum, and the system has a vacuum degree of 0.001 KPa to 100 KPa, and preferably of 1 KPa to 60 KPa.

Compared with the prior art, the method for preparing a dialkyl carbonate by alcoholysis of urea provided in the present invention has the following advantages and features:

(1) A dialkyl carbonate is prepared with urea as a raw material, with high selectivity and high yield. In particular, a corresponding dialkyl carbonate is prepared by reacting urea with low-boiling methanol or ethanol.
(2) The adopted catalyst has low toxicity, high safety and low cost.
(3) The reaction is conducted at a lower temperature under normal pressure or reduced pressure, with simple and safe operations.
(4) The process requires low energy consumption and low operating costs.
(5) The cost of process equipment is low.

It can be seen from above descriptions that the method for preparing a dialkyl carbonate by alcoholysis of urea provided in the present invention has prominent industrial application prospects.

DETAILED DESCRIPTION OF THE EMBODIMENTS

The present invention is described below in conjunction with specific examples, which facilitates the further understanding of the advantages and effects of the present invention. The protection scope of the present invention is not limited by the examples, and is determined by claims.

EXAMPLE 1

The reaction device included a 200 ml three-necked glass flask, a rectification column and a condenser. The rectification column had a diameter of 30 mm and a length of 300 mm and was filled with a 2 mm×2 mm stainless steel θ ring. 10 g of urea, 22 g of methanol, 50 g of sulfolane, 0.5 g of nickel acetate and 2 g of triphenylphosphine were added to the three-necked flask and heated under a 170° C. oil bath. The system reacted at 85° C. for 10 h under boil, stirring and reflux. The light component was removed from the system, then condensed, and flowed into a receiver. The system was heated to 130° C., and the light component in the receiver was injected into the reaction flask to maintain the receiver liquid level. The system reacted at 130° C. to 150° C. for 15 h under stirring and reflux. With gas chromatography, based on the amount of urea added, the yield of dimethyl carbonate was 89.3%, and no methyl N-methyl formate was detected in the system.

EXAMPLE 2

The reaction device was the same as Example 1. 10 g of urea, 31 of ethanol, 50 g of sulfolane, 0.5 g of nickel acetate and 2 g of triphenylphosphine were added to the three-necked flask and heated under a 170° C. oil bath. The system reacted at 95° C. for 8 h under boil, stirring and reflux. The light component was removed from the system, then condensed, and flowed into a receiver. The system was heated to 130° C., and the light component in the receiver was injected into the reaction flask to maintain the receiver liquid level. The system reacted at 130° C. to 150° C. for 15 h under stirring and reflux. With gas chromatography, based on the amount of urea added, the yield of diethyl carbonate was 92.4%.

EXAMPLE 3

The reaction device was the same as Example 1. 10 g of urea, 40 g of n-propanol, 0.5 g of nickel acetate and 2 g of triphenylphosphine were added to the three-necked flask, and heated under a 170° C. oil bath. The system reacted at 105° C. for 8 h under boil, stirring and reflux. The system was then heated to 130° C. The system reacted at 130° C. to 150° C. for 15 h under stirring and reflux. With gas chromatography, based on the amount of urea added, the yield of di-n-propyl carbonate was 93.6%.

EXAMPLE 4

The reaction device was the same as Example 1. 10 g of urea, 50 g of n-butanol, 0.5 g of nickel acetate and 2 g of triphenylphosphine were added to the three-necked flask, and heated under a 170° C. oil bath. The system reacted at 110° C. for 20 h under boil, stirring and reflux. With gas chromatography, based on the amount of urea added, the yield of di-n-butyl carbonate was 95.0%.

EXAMPLE 5

The reaction device was the same as Example 1. 10 g of urea, 60 g of n-pentanol, 0.5 g of nickel acetate and 2 g of triphenylphosphine were added to the three-necked flask, and heated under a 170° C. oil bath. The system reacted at 140° C. for 20 h under boil, stirring and reflux. With gas chromatography, based on the amount of urea added, the yield of di-n-pentyl carbonate was 92.2%.

EXAMPLE 6

The reaction device was the same as Example 1. 10 g of urea, 68 g of n-hexanol, 0.5 g of nickel acetate and 2 g of triphenylphosphine were added to the three-necked flask, and heated under a 170° C. oil bath. The system was placed under vacuum to have a vacuum degree of 10 KPa; and the system reacted at 110° C. for 20 h under gentle boil, stirring and reflux. With gas chromatography, based on the amount of urea added, the yield of di-n-hexyl carbonate was 92.3%.

EXAMPLE 7

The reaction device was the same as Example 1. 10 g of urea, 78 g of n-heptanol, 0.5 g of nickel acetate and 2 g of triphenylphosphine were added to the three-necked flask, and heated under a 170° C. oil bath. The system was placed under vacuum to have a vacuum degree of 20 KPa; and the system reacted at 140° C. for 20 h under stirring and reflux. With gas chromatography, based on the amount of urea added, the yield of di-n-heptyl carbonate was 91.8%.

EXAMPLE 8

The reaction device was the same as Example 1. 10 g of urea, 87 g of n-octanol, 0.5 g of nickel acetate and 2 g of triphenylphosphine were added to the three-necked flask, and heated under a 170° C. oil bath; the system was placed under vacuum to have a vacuum degree of 20 KPa; and the system reacted at 140° C. for 20 h under stirring and reflux. With gas chromatography, based on the amount of urea added, the yield of di-n-octyl carbonate was 90.6%.

What is claimed is:

1. A method for preparing a dialkyl carbonate by alcoholysis of a urea, comprising
reacting the urea with an alkyl monohydric alcohol ROH ($R=C_nH_{2n+1}$, with n=1 to 12), with one or more of magnesium, calcium, aluminum, chromium, manganese, iron, cobalt, nickel, copper and zinc as a primary catalyst, and one or more compounds with one or more of electron-donating nitrogen, phosphorus, oxygen and sulfur atoms as a catalyst promoter,
wherein an ammonia is produced during the reaction; the primary catalyst and the catalyst promoter are used at a mass ratio of 1:(1-20); the urea and the alkyl monohydric alcohol are used at a molar ratio of 1:(2-10); the amount of the catalyst is 5 to 40 mass % to urea; and the reaction is conducted at 70° C. to 150° C. for a period of 6 h to 30 h, and wherein
a solvent is added to the reaction, the solvent is one or more selected from the group consisting of C8-18 alkane, biphenyl, diphenyl ether, sulfolane and dimethyl sulfone, and the solvent is added at a mass ratio of (1-20):1 to the urea.

2. The method according to claim 1, wherein the primary catalyst is one or more selected from the group consisting of chloride, bromide, sulfate, perchlorate, nitrate and carboxylate M(RCOO)q, wherein M is Mg, Ca, Al, Cr, Mn, Fe, Co, Ni, Cu or Zn, q=2 or 3, $R=C_nH_{2n+1}$, and n=0 to 6, of Mg (II), Ca (II), Al (III), Cr (II, III), Mn (II), Fe (II, III), Co (II), Ni (II), Cu (II) or Zn (II).

3. The method according to claim 1, wherein, the catalyst promoter is one or more selected from the following:
(1) compounds with an electron-donating nitrogen atom:
(i) monoamine compound

wherein, $R_1$, $R_2$ and $R_3$ are each hydrogen, alkyl or aryl, and there are no more than 20 carbon atoms;
(ii) alkyl or aryl diamine and triamine compounds, wherein there are no more than 20 carbon atoms; and
(iii) nitrogen-containing heterocyclic compounds;
(2) compounds with an electron-donating phosphorus atom:
trivalent organic phosphine compound

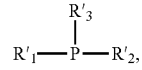

wherein $R'_1$, $R'_2$, and $R'_3$ are each alkyl or aryl, and there are no more than 30 carbon atoms;
(3) compounds with an electron-donating oxygen atom:
(i) alkyl or aryl ether, wherein there are no more than 20 carbon atoms;
(ii) alkyl or aryl carboxylate ester, wherein there are no more than 20 carbon atoms;
(iii) alkyl or aryl carboxylate salt, wherein there no more than 20 carbon atoms, and the metal is an alkali metal; and
(iv) oxygen-containing heterocyclic compounds;
(4) compounds with an electron-donating sulfur atom:
(i) alkyl or aryl sulfide, wherein there are no more than 20 carbon atoms; and
(ii) sulfur-containing heterocyclic compounds;
(5) compounds with two or more of electron-donating nitrogen, phosphorus, oxygen and sulfur atoms:
(i) amino acid;
(ii) amino (amine) carboxylic acid; and
(iii) amino (amine) phosphonic acid; and
(6) heterocyclic compounds with two electron-donating atoms.

4. The method according to claim 1, wherein the urea reacts with a low-boiling alkyl alcohol ROH (R=$C_nH_{2n+1}$, and n=1 or 2).

5. The method according to claim 1, wherein when n=1 to 5 the urea reacts with the alkyl monohydric alcohol ROH under atmospheric pressure; and when n=6 to 12 the urea reacts with the alkyl monohydric alcohol ROH under a vacuum, having a degree of 0.001 KPa to 100 KPa.

\* \* \* \* \*